US00PP37582P2

(12) United States Plant Patent
Knoblauch

(10) Patent No.: US PP37,582 P2
(45) Date of Patent: Aug. 11, 2026

(54) ***BEGONIA* PLANT NAMED 'BEYZ0008'**

(50) Latin Name: *Begonia hybrida*
Varietal Denomination: BEYZ0008

(71) Applicant: SYNGENTA CROP PROTECTION AG, Basel (CH)

(72) Inventor: Cathy Knoblauch, Whitecourt (CA)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/293,067

(22) Filed: Aug. 7, 2025

(51) Int. Cl.
*A01H 5/02* (2018.01)
*A01H 5/12* (2018.01)
*A01H 6/18* (2018.01)

(52) U.S. Cl.
USPC ..... Plt./343
CPC ..... *A01H 6/185* (2018.05); *A01H 5/02* (2013.01); *A01H 5/12* (2013.01)

(58) Field of Classification Search
USPC ..... Plt./343
See application file for complete search history.

(56) References Cited

U.S. PATENT DOCUMENTS

PP35,262 P2 * 7/2023 Koot ..... A01H 6/18
Plt./343

OTHER PUBLICATIONS https://www.floraldaily.com/article/9663510/US-icandy-begonias-available-for-pre-release/ (Retrieved online Oct. 14, 2025) (Year: 2024).*

* cited by examiner

*Primary Examiner* — Susan Mccormick Ewoldt
*Assistant Examiner* — Zachariah Allan Kay
(74) *Attorney, Agent, or Firm* — Dale Skalla

(57) ABSTRACT

A new *Begonia* plant named 'BEYZ0008' characterized by its compact symmetrical rounded habit, double yellow to orange male flowers, and single yellow to orange female flowers that bloom from spring to fall. 'BEYZ0008' is also characterized by its deep mahogany foliage with bright green veins.

1 Drawing Sheet

Botanical designation: *Begonia hybrida.*
Cultivar denomination: 'BEYZ0008'.

BACKGROUND OF THE NEW PLANT

The present invention comprises a new *Begonia* plant, botanically known as *Begonia hybrida*, and hereinafter referred to by the variety name 'BEYZ0008'.

'BEYZ0008' is a product of a planned breeding program in Whitecourt, Alberta, Canada. The new cultivar 'BEYZ0008' has a compact symmetrical rounded habit, double yellow to orange male flowers, and single yellow to orange female flowers that bloom from spring to fall. 'BEYZ0008' is also characterized by its deep mahogany foliage with bright green veins.

'BEYZ0008' is the result of a planned pollination conducted at the inventor's nursery at Whitecourt, Alberta made in August 2019. The female parent of the new cultivar is the unnamed yellow seedling of proprietary origin, unpatented, and characterized by its dark foliage and larger flowers. 'BEYZ0008' differs from the unnamed yellow seedling of the inventor's proprietary selection by having a bicolored yellow and orange flower. The male parent of the new cultivar is the unnamed seedling of the proprietary selection, unpatented, having a larger flower and a larger overall plant size than 'BEYZ0008'.

The resulting seed was sown in Whitecourt, Alberta, Canada in a controlled greenhouse environment in 2020 and 'BEYZ0008' was selected as one flowering plant within the progeny of the stated cross in June 2020.

The first act of asexual reproduction of 'BEYZ0008' was accomplished when vegetative stem cuttings were propagated from the initial selection in the inventor's nursery, in Whitecourt, Alberta, Canada.

BRIEF SUMMARY OF INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

A Plant Breeder's Right for this cultivar has not yet been applied for. 'BEYZ0008' has not been made publicly available prior to the effective filing date of this application, notwithstanding any disclosure that may have been made less than one year prior to the effective filing date of this application by the inventor or another who obtained 'BEYZ0008' directly from the inventor.

The following traits have been repeatedly observed and are determined to be basic characteristics of the new variety. The combination of these characteristics distinguishes this *Begonia* as a new and distinct variety.

BRIEF DESCRIPTION OF THE PHOTOGRAPHS

Figure 1:
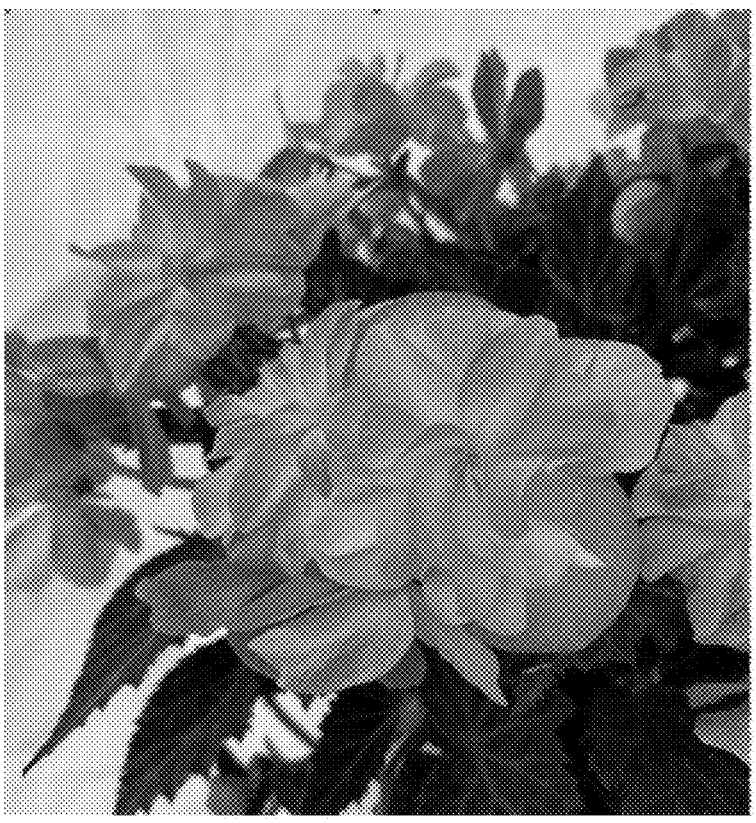
Figure 2:
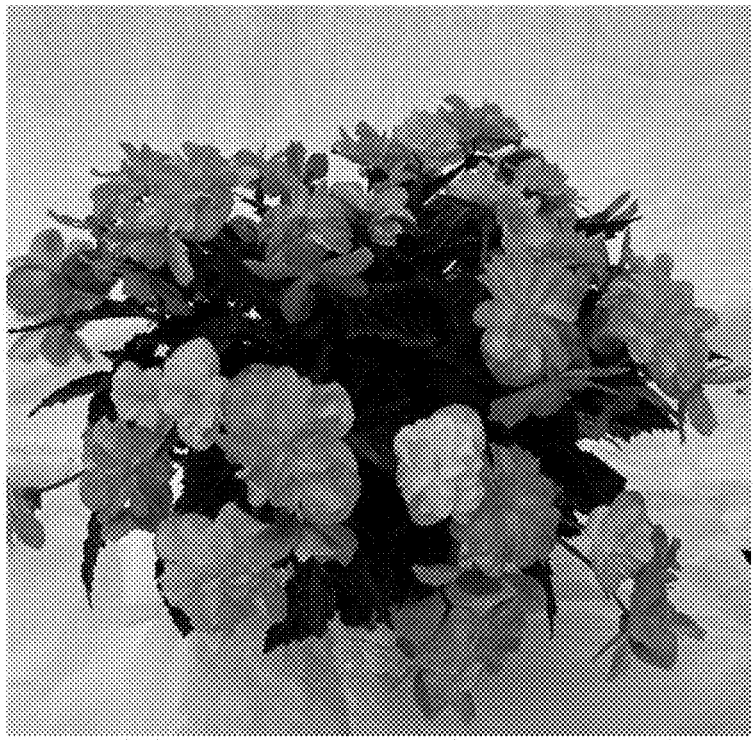

The accompanying photographic drawings show typical flower and foliage characteristics of 'BEYZ0008' with colors being as true as possible with an illustration of this type. The photographic drawings show in FIG. 1 a close view of an inflorescence taken in Whitecourt, Alberta, Canada in June 2025, and in FIG. 2 a whole flowering plant taken in Whitecourt, Alberta, Canada in June 2025.

DETAILED BOTANICAL DESCRIPTION

The plant descriptions and measurements were taken in Whitecourt, Alberta in June 2025. The plants were approximately 4 months old and were growing in 8 inch pots, one plant per pot in the inventor's greenhouse under natural light in Whitecourt, Alberta in the summer of 2025

Color references are made to The Royal Horticultural Society Colour Chart (R.H.S.) 2001.

Traits

1. 'BEYZ0008' has a mounded compact and symmetrical habit
2. 'BEYZ0008' achieves a height of about 25 cm
3. 'BEYZ0008' achieves a width of about 30 cm
4. 'BEYZ0008' blooms continuously from spring until fall
5. 'BEYZ0008' is self branching and achieves a height of about 25 cm and a width of about 30 cm in a growing season from spring to fall.
6. 'BEYZ0008' exhibits fully double flowers that are multiple colors of yellow, orange pink, and peach.
7. 'BEYZ0008' exhibits deep brown chocolate colored foliage with deep red undersides.

TABLE 1

DIFFERENCES BETWEEN THE NEW VARIETY 'BEYZ0008' AND A MOST SIMILAR VARIETY

| | 'BEYZ0008' | 'On Top Sunset Shade', not patented |
|---|---|---|
| Flower and leaf size: | Smaller leaf and flower size | Larger leaf and flower size |
| Foliage: | Darker mahogany brown | Green |
| Basal and lateral branching: | Natural and prolific | Slow branching, asymmetrical habit |

Propagation:

*Type*.—Vegetative tip cuttings.

*Time to initiate roots, summer and winter*.—10 days summer, 15 days winter.

*Time to produce a rooted young plant summer*.—8 weeks.

*Time to produce a rooted young plant, winter*.—10 weeks.

*Root description*.—Self branching and achieving a depth of approximately 20 cm and a width of approximately 30 cm in a growing season from spring to fall.

*Rooting habit*.—Freely branching.

Plant description:

*Plant and growth habit*.—Upright, mounded and freely branching.

*Plant height, soil level to top of foliar plane*.—About 22 cm.

*Plant height, soil level to top of floral plane*.—About 25 cm.

*Plant width*.—About 30 cm.

*Lateral branch description*.—Upright, freely branching.

*Length*.—About 16 cm.

*Stem diameter*.—About 8 mm.

*Internode length*.—About 3 cm.

*Aspect*.—Upright, symmetrical.

*Texture and luster*.—Smooth, matte.

*Color, developing, foliage*.—RHS 171A through RHS 199C.

*Color, developed, flower*.—RHS 14A through RHS 28A.

Leaf description:

*Arrangement*.—Alternate.

*Length*.—About 8 cm.

*Width*.—About 5 cm.

*Shape*.—Asymmetrical.

*Apex*.—Acute.

*Base*.—Obtuse.

*Margin*.—Double serrate.

*Texture and luster, upper and lower surfaces*.—Coriaceous, matte.

*Venation pattern*.—Palmate.

*Developing leaves, upper surface*.—Palmate.

*Developing leaves, lower surface*.—Palmate.

*Fully expanded leaves, upper surface*.—Palmate.

*Fully expanded leaves, lower surface*.—Palmate.

Petioles:

*Length*.—About 4 cm.

*Diameter*.—About 5 mm.

*Texture and luster, upper and lower surfaces*.—Pilose, brittle.

*Color, upper surface*.—Nearest to RHS 131A.

*Color, lower surface*.—Nearest to RHS 178B.

Stipules:

*Quantity per leaf*.—One.

*Length*.—1 cm.

*Width*.—5 mm.

*Shape*.—Triangular.

*Apex*.—Sharply acute.

*Base*.—Broadly triangular.

*Margins*.—Entire.

*Color, upper and lower surfaces*.—Nearest to RHS 146D.

Flower description:

*Flowering habit*.—Continuous.

*Fragrance*.—None.

*Natural flowering season*.—Spring to fall.

*Flower longevity*.—About 30 days.

*Inflorescence height* (*including peduncle*).—About 10 cm.

*Flower buds, female flowers*.—

*Length*.—About 2.5 cm.

*Diameter, flattened*.—About 2.5 cm.

*Shape*.—Broadly obovate.

*Texture and luster*.—Smooth, semi glossy.

*Color, upper surface*.—RHS 30C.

*Color, lower surface*.—RHS 4C.

*Flower buds, male flowers*.—

*Length*.—About 3 cm.

*Diameter, flattened*.—About 3 cm.

*Shape*.—Broadly obovate.

*Texture and luster*.—Smooth, semi glossy.

*Color, upper surface*.—RHS 33A.

*Color, lower surface*.—RHS 3B through RHS 28A.

*Female flowers size*.—Length About 9 cm.

*Depth*.—About 8 cm.

Tepals, female:

*Quantity per flower and arrangement.*—5, arranged in a single whorl.

*Length, female tepals.*—About 4 cm.

*Width, female tepals.*—About 2 cm.

*Shape, female tepals.*—Obovate.

*Apex.*—Female tepals: Broadly ovate.

*Base, female tepals.*—

*Margin, female tepals.*—Entire.

*Texture and luster, female tepals, upper surface.*—Smooth, semi glossy.

*Texture and luster, female tepals, lower surface.*—Smooth, glossy.

*Color, female tepals.*—

*When opening, upper surface.*—RHS 8A through RHS 8C.

*When opening, lower surface.*—Nearest to RHS 15D.

*Fully opened, upper surface.*—RHS 14A through RHS 28A.

*Fully opened, lower surface.*—RHS 14A through RHS 28A.

*Color, outer tepals.*—No outer tepals, female flowers are a single whorl of 5 tepals.

*When opening, female tepals upper surface.*—RHS 8A through RHS 8C.

*When opening, female tepals lower surface.*—Nearest to RHS 30C.

*Fully opened, female tepals upper surface.*—Nearest to RHS 34D.

*Fully opened, female tepals lower surface.*—Nearest to RHS 32A.

*Tepaloids.*—None observed on female flowers.

*Male flowers.*—

*Size.*—Width male flowers: About 8 cm.

*Depth.*—Male flowers: About 8 cm.

Tepals:

*Quantity per flower and arrangement.*—About 50 arrange in about 6 separate whorls.

*Length, male inner tepals.*—About 2.5 cm.

*Length, male outer tepals.*—About 3.5 cm.

*Width, male inner tepals.*—About 2 cm.

*Width, male outer tepals.*—About 4 cm.

*Shape, male inner tepals.*—Obovate.

*Shape, male outer tepals.*—Circular.

*Apex, male inner and outer tepals.*—Obovate, circular.

*Base, male inner and outer tepals.*—Narrowly obovate.

*Margin, male inner and outer tepals.*—Entire.

*Texture and luster, male inner and outer tepals, upper surface.*—Smooth, semi glossy.

*Texture and luster, male inner and outer tepals, lower surface.*—Smooth, semi glossy.

*Color, male inner tepals.*—

*When opening, upper surface.*—RHS 9B through RHS 34B.

*When opening, lower surface.*—Nearest to RHS 15D.

*Fully opened, upper surface.*—Nearest to RHS 7B.

*Fully opened, lower surface.*—Nearest to RHS 10B.

*Color, male outer tepals.*—

*When opening, upper surface.*—Nearest RHS 8A.

*When opening, lower surface.*—Nearest RHS 5C.

*Fully opened, upper surface.*—Nearest RHS 9A.

*Fully opened, lower surface.*—RHS 8B through RHS 30C.

*Tepaloids.*—None observed on male flowers.

Peduncles:

*Length.*—About 8 cm.

*Diameter.*—About 5 mm.

*Angle.*—Upright.

*Texture and luster.*—Smooth, semi glossy.

*Color, upper surface.*—Nearest RHS 166B.

*Color, lower surface.*—Nearest RHS 152C.

Pedicels, female flowers:

*Length.*—About 2 cm.

*Diameter.*—About 2 mm.

*Angle.*—Moderately pendulous.

*Texture and luster.*—Smooth, glossy.

*Color, upper surface.*—Nearest to RHS 30C.

*Color, lower surface.*—Nearest to RHS 32D.

Pedicels, male flowers:

*Length.*—About 2.5 cm.

*Diameter.*—About 3 mm.

*Angle.*—About 45 degrees.

*Texture and luster.*—Smooth, glossy.

*Color, upper surface.*—Nearest to RHS 30C.

*Color, lower surface.*—Nearest to RHS 21A.

Flower bracts:

*Quantity per flower and arrangement.*—2, opposite.

*Length.*—About 1 cm.

*Width.*—About 1 cm.

*Shape.*—Obovate.

*Apex.*—Broadly ovate.

*Base.*—Broadly ovate.

*Margin.*—Scabrous.

*Texture and luster, upper and lower surfaces.*—Smooth, semi glossy.

*Color, upper surface.*—Nearest to RHS 146D.

*Color, lower surfaces.*—Nearest to RHS 46A.

Reproductive organs:

Androecium:

*Stamen quantity per flower.*—None observed.

*Filament length.*—N/A.

*Filament color.*—N/A.

*Anther size.*—N/A.

*Anther shape.*—N/A.

*Anther color.*—N/A.

*Amount of pollen.*—N/A.

*Pollen color.*—N/A.

Gynoecium:

*Quantity per flower.*—One.

*Pistil length.*—About 1 cm.

*Stigma diameter.*—About 1 cm.

*Stigma shape.*—Bifurcated, three tight spirals.

*Stigma color.*—Nearest to RHS 17C.

*Style length.*—About 2 mm.

*Style color.*—Nearest to RHS 16B.

*Ovary color.*—Nearest to 31A.

*Seeds and fruits.*—None observed.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 30° C. and to be suitable for USDA Hardiness Zones 7 to 9.

What is claimed is:

1. A new and distinct variety of *Begonia* plant named 'BEYZ0008' substantially as illustrated and described herein.

* * * * *